United States Patent [19]

van Duyn

[11] Patent Number: Plant 6,752

[45] Date of Patent: Apr. 25, 1989

[54] ALSTROEMERIA NAMED CYPRUS

[75] Inventor: Cornelis van Duyn, NA Rijnsburg, Netherlands

[73] Assignee: Groot Associates II, Irvine, Calif.

[21] Appl. No.: 57,235

[22] Filed: Jun. 1, 1987

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Jackson & Jones

[57] ABSTRACT

A new Alstroemeria variety characterized by the pale colored blossoms, the outer petals of which are yellowish white and inner petals of which are deep yellow with a yellow striped heart with flecks of purplish red. The plant is early in flowering with relatively short stems.

1 Drawing Sheet

BACKGROUND OF THE NEW PLANT

This new Alstroemeria originated as a sport at Rijnsburg, Holland. The particular sport was selected from plants propagated via root divisions by me in 1982 for propagation and testing because of the distinctive coloration of its blossoms produced on upright compact stems. Specifically, the inner petals are deep yellow with yellow striped hearts. The outer petals are light yellow with purplish pink toward the top. The inner petals have well defined longitudinal streaks or flecks of purplish red. The selected plant was propagated by me at Rijnsburg. Holland through several generations of root divisions to establish that its distinctive characteristics hold true from generation to generation and appear to be firmly fixed.

Breeding efforts commenced in 1980 and propagation is currently being carried out at Rinjsburg, Holland. The nearest variety is the Alstroemeria called Walter Fleming and my new variety, Cyprus, differs from the Walter Fleming in that (1) the outer petals are yellower with a slight purple coloring towards the top, (2) the filaments are light purplish-pink and (3) the plant is earlier in flowering.

DESCRIPTION OF THE DRAWING

This new variety of the Alstroemeria plant is illustrated by the accompanying photograph which shows a blooming umbel of the plant with buds and flowers in various stages of opening.

DESCRIPTION OF THE NEW PLANT

The following is a detailed description of my new Alstroemeria plant with color designations according to The National Bureau of Standards, Standard Reference Material, #2107, comprising the ISCC-NBS Centroid Color Charts and NBS Special Publication, #440.

THE PLANT

Origin: Sport.
Parentage: Walter Fleming.
Classification: Orchid type.
Form: A generally erect bush having an upright stalk with flower-bearing branches in simple umbel arrangement at its top.
Height: About 1.60 meters.
Growth: Upright and normal.
Root stock: Mutation.

Foliage:
- *Quantity.*—Normal.
- *Number of leaves.*—About 35–40 per stem.
- *Size of leaf.*—About 12 cm×3 cm.
- *Shape of leaf.*—Parallel venation.
- *Texture.*—Smooth.
- *Color.*—Upper side: Light green. Under side: Light green.

THE BUD

Form: Long, ovoid.
Size: Medium.
- *Diameter.*—About 1.2 cm.
- *Length.*—About 3 cm.

Peduncle:
- *Length.*—About 14.5 cm.
- *Texture.*—Smooth.
- *Form.*—Erect.

THE FLOWER

Blooming habit: Profusely during early season in Spring.
Flower size: Medium to small.
- *Diameter.*—About 5.5 cm.
- *Depth.*—About 4 cm.

Borne: Terminal clusters.
Shape: Generally cup shaped with petal tips curling outwardly.
Petalage:
- *Number of petals.*—Six.
- *Arrangement.*—Two concentric circles of three.
- *Form.*—Broad ovate.
- Texture.—Soft.
- *Appearance.*—Satiny.

Color:
- *Outer petals.*—Pale yellow (No. 89) with light yellow (No. 83) (center) and light reddish purple tip (No. 256).
- *Inner petals.*—Dark yellow (No. 82) with a striped heart. The inner petals have numerous generally longitudinal strips or flecks of very deep purplish red (No. 260).

Persistence: The flowers hang on and dry.
Main stem or stalk:
- *Length.*—About 14.5 cm.
- *Color.*—Light green.
- *Character.*—Strong and upright.

Lasting quality of flower: About 3 weeks. As a cut flower, about 14 days.

REPRODUCTIVE ORGANS

Stamens:
*Number.*—Six.
*Arrangement.*—One opposite each petal.
Anthers:
*Size.*—About 0.7 cm×0.2 cm.
*Color.*—Grayish yellow green (No. 122).
Filaments:
*Length.*—About 3.7 cm.
*Color.*—Pale purplish pink (No. 252).
*Pollen.*—Yellow grey.
Pistils:
*Number.*—One.
*Styles.*—Length: About 3.7 cm. Color: Pale Purplish Pink (No. 252).

Fruit:
*Shape.*—Oblong.
*Color.*—Light brown.

This plant is particularly noted for the distinctive coloration of its flowers, which coloration does not clearly resemble that of any other Alstroemeria plant previously known to me. The very deep purplish red flecks on the dark yellow inner petals with the striped hearts and outer petals with the yellowish white coloring with light yellow (center) makes this plant an attractive addition to the Alstroemeria family.

I claim:

1. A new and distinctive Alstroemeria cultivar, substantially as herein shown and described, characterized by the distinctive coloration of its medium to small and profusely blooming flowers.

* * * * *

U.S. Patent Apr. 25, 1989 Plant 6,752
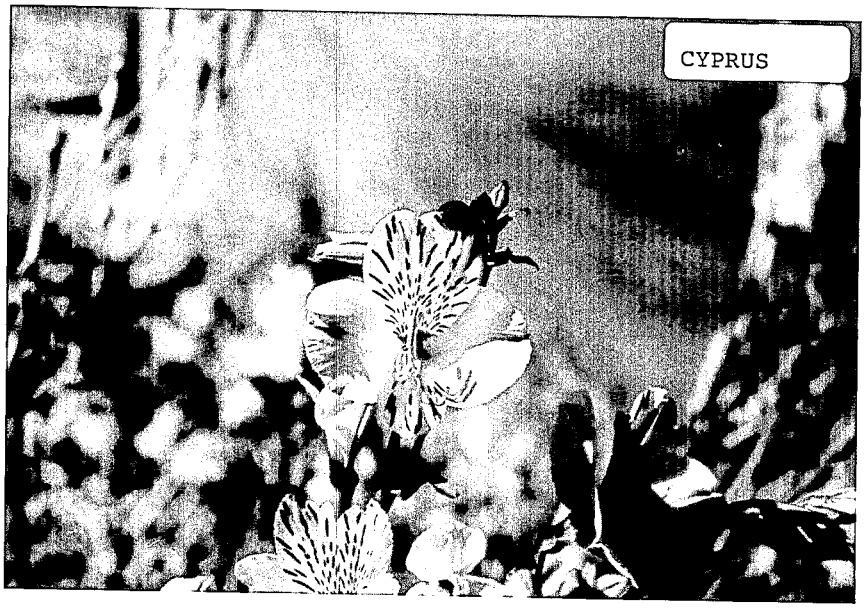

UNITED STATES PATENT AND TRADEMARK OFFICE

CERTIFICATE OF CORRECTION

PATENT NO. : Plant 6,752

DATED : April 25, 1989

INVENTOR(S) : Cornelis van Duyn

It is certified that error appears in the above—identified patent and that said Letters Patent is hereby corrected as shown below:

Column 2, line 42, after "longitudinal" delete "strips" and insert --stripes--.

Signed and Sealed this

Second Day of January, 1990

*Attest:*

JEFFREY M. SAMUELS

*Attesting Officer*

*Acting Commissioner of Patents and Trademarks*